US006981988B1

(12) United States Patent
Kinsley

(10) Patent No.: US 6,981,988 B1
(45) Date of Patent: Jan. 3, 2006

(54) BREAST IMPLANT SIZING SYSTEM

(76) Inventor: Elizabeth Kinsley, 230 Bigner Rd., Mandeville, LA (US) 70471

( * ) Notice: Subject to any disclaimer, the term of this patent is extended or adjusted under 35 U.S.C. 154(b) by 151 days.

(21) Appl. No.: 10/093,900

(22) Filed: Mar. 8, 2002

(51) Int. Cl.
*A61F 2/12* (2006.01)
*A61B 5/10* (2006.01)
*A43D 8/28* (2006.01)
*G01B 3/14* (2006.01)
*G01F 17/00* (2006.01)

(52) U.S. Cl. .............................. 623/8; 623/7; 600/587; 33/2 R; 33/562; 33/512; 73/149

(58) Field of Classification Search ................ 623/8, 623/7, 66; 33/174, 2 R, 562, 511, 512; 75/149; 600/587; 73/149
See application file for complete search history.

(56) References Cited

U.S. PATENT DOCUMENTS

| 3,896,506 A | * | 7/1975 | Hankin et al. ................ 623/7 |
| 4,024,856 A | * | 5/1977 | Kirianoff .................... 600/587 |
| 4,095,295 A | * | 6/1978 | Lake ............................ 623/8 |
| 4,125,117 A | * | 11/1978 | Lee .............................. 450/57 |
| 4,219,029 A | * | 8/1980 | Grossman et al. .......... 600/587 |
| 4,279,259 A | * | 7/1981 | Lee et al. ................... 600/587 |
| 4,605,412 A | * | 8/1986 | LaForest et al. .............. 623/8 |
| 5,236,454 A | * | 8/1993 | Miller ............................ 623/8 |
| 5,340,352 A | * | 8/1994 | Nakanishi et al. ............. 450/57 |
| 5,695,445 A | * | 12/1997 | Khouri ........................ 600/38 |
| 6,055,989 A | * | 5/2000 | Rehnke ....................... 128/898 |
| 6,101,630 A | * | 8/2000 | Lee ................................ 2/57 |
| 6,430,446 B1 | * | 8/2002 | Knowlton .................... 607/101 |

OTHER PUBLICATIONS

Pechter, Edward "A New Mthod for Determining Bra Size and Predicting Post Augmentation Breast Size", Apr. 11, 2003.*
www.justbreastimplants.com; 2001.*
JustBreastimplants.com ,"Jill's Breast Augmentation Story"; Jan. 2001.*
Dowden, Richard MD. "How is the correct implant size determined?", www.dr-dowden.com; Aug. 1999.*

* cited by examiner

*Primary Examiner*—David J. Isabella
(74) *Attorney, Agent, or Firm*—Jones, Waker, Waechter, Poitevent, Carrere & Denegre, L.L.P.

(57) ABSTRACT

A method for selecting a properly sized breast implant by first providing a breast ruler, at least one pair of flexible, fillable implant devices, and a liquid measuring device adapted to fill the implant devices. Next, the breast ruler is placed over a breast of a user and a breast width is measured. Then the liquid measuring device is used to fill the implant devices with an approximate amount of liquid corresponding to the earlier measured breast width. Then the filled implants are placed over the breasts with an item of clothing. Finally, the amount of liquid in the implant devices may be adjusted for the desired breast size and appearance.

8 Claims, 4 Drawing Sheets

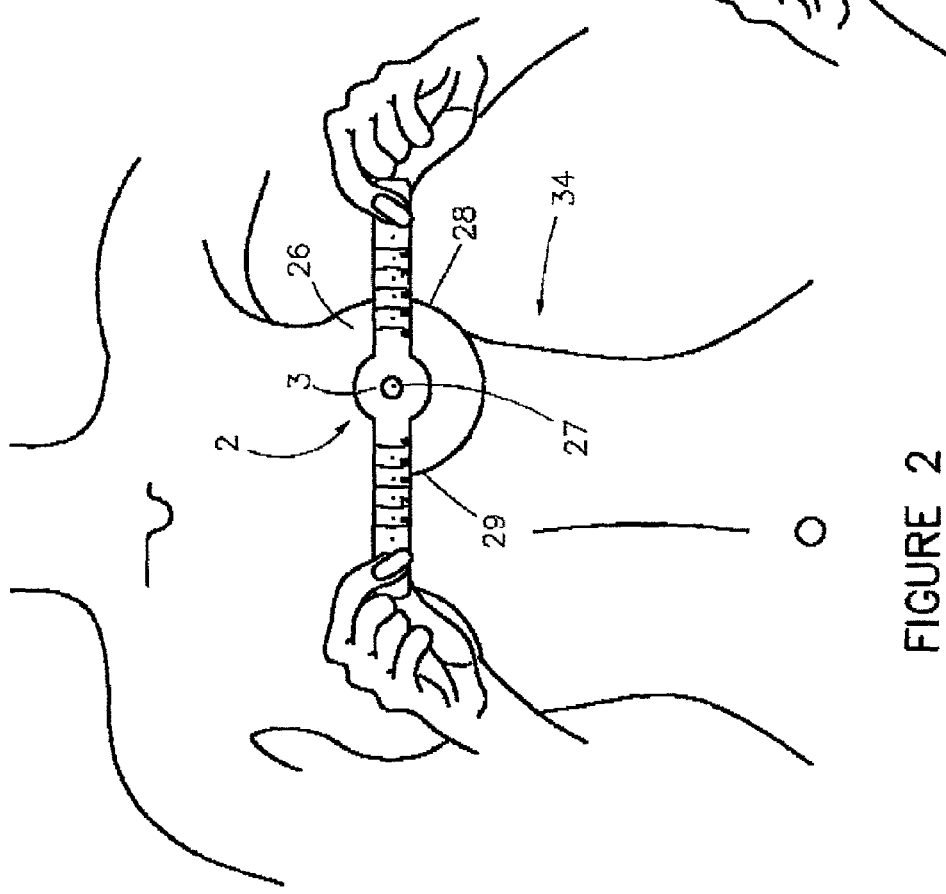
FIGURE 2
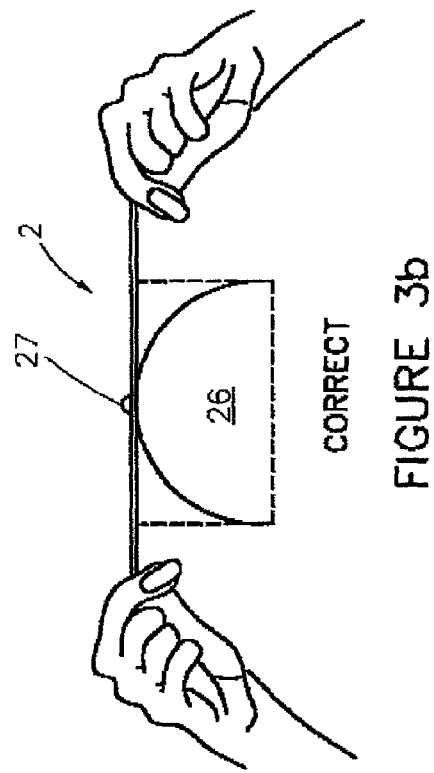
INCORRECT
FIGURE 3A
CORRECT
FIGURE 3b

BREAST IMPLANT SIZING SYSTEM

BACKGROUND OF INVENTION

The present invention relates to breast implants. In particular, the present invention relates to a method for allowing a person contemplating implant surgery to determine what size of implant appears most suitable to that person.

Breast implants are manufactured in a range of sizes and it is imperative for the patient to be provided with the size implants that the patient believes most suits her appearance. The present state of the art for sizing breast implants typically consists of the patient and physician making a determination of implant size in the physician's office. The patient's height, weight, and breast size will be measured and the physician will, user his or her experience and judgment to suggest a likely implant size for that patient's physical characteristics. However, this procedure does not lend itself to maximizing the patient's input on the ultimate decision of implant sizing. Even if the patient was allowed to "try on" implants in the physician's office by positioning the implants within the patient's bra and observing the appearance, this would have several drawbacks. First, the patient is limited in the time available to study the appearance of different implants since this procedure would take place in a busy physician's office. Second, the patient may wish to view the "try on" implants in combination with various articles of clothing to more fully determine how the implants will affect the patient's appearance. Nevertheless, it obviously is not be practical for the patient to bring an entire wardrobe to the physician's office, so the patient would have to forgo the advantage of viewing the implants with various items of clothing. Third, the patient may wish to consult family or friends as to which size implants gives the most favorable appearance, but again, this normally will not be practical in the physician's office. Finally, no matter how friendly and relaxed of an environment the physician may attempt to promote in his or her office, it cannot substitute for the privacy of the patient's home when viewing the appearance of the implants.

It would be a significant advance in the art if a method of selecting an implant size could be developed which overcomes these disadvantages. The method should be implemented with a kit which may be inexpensively manufactured and therefore made widely available. The method should be simple enough that persons with no special knowledge or training may practice the method in the privacy of their home. And finally, the method should provide patients with the ability to realistically determine how a range of implant sizes will change their appearance.

SUMMARY OF INVENTION

The present invention provides a method for selecting a properly sized breast implant. The method includes providing a breast ruler, at least one pair of flexible, fillable implant devices, and a liquid measuring device adapted to fill the implant devices. The breast ruler is first placed over the breast of a user in order to measure the breast width. The liquid measuring device is next used to fill the implant devices with an approximate amount of liquid corresponding to the breast width. The user then positions the filled implants over the breasts with an item of clothing. Finally, the user may adjust the amount of liquid in the implant devices in order to obtain the breast size and appearance desired.

BRIEF DESCRIPTION OF THE DRAWINGS

FIG. 2 illustrates the breast ruler being used to measure the breast width.

FIGS. 3a and 3b illustrate correct and incorrect manners of measuring the breast width.

DETAILED DESCRIPTION OF INVENTION

Figure 1:
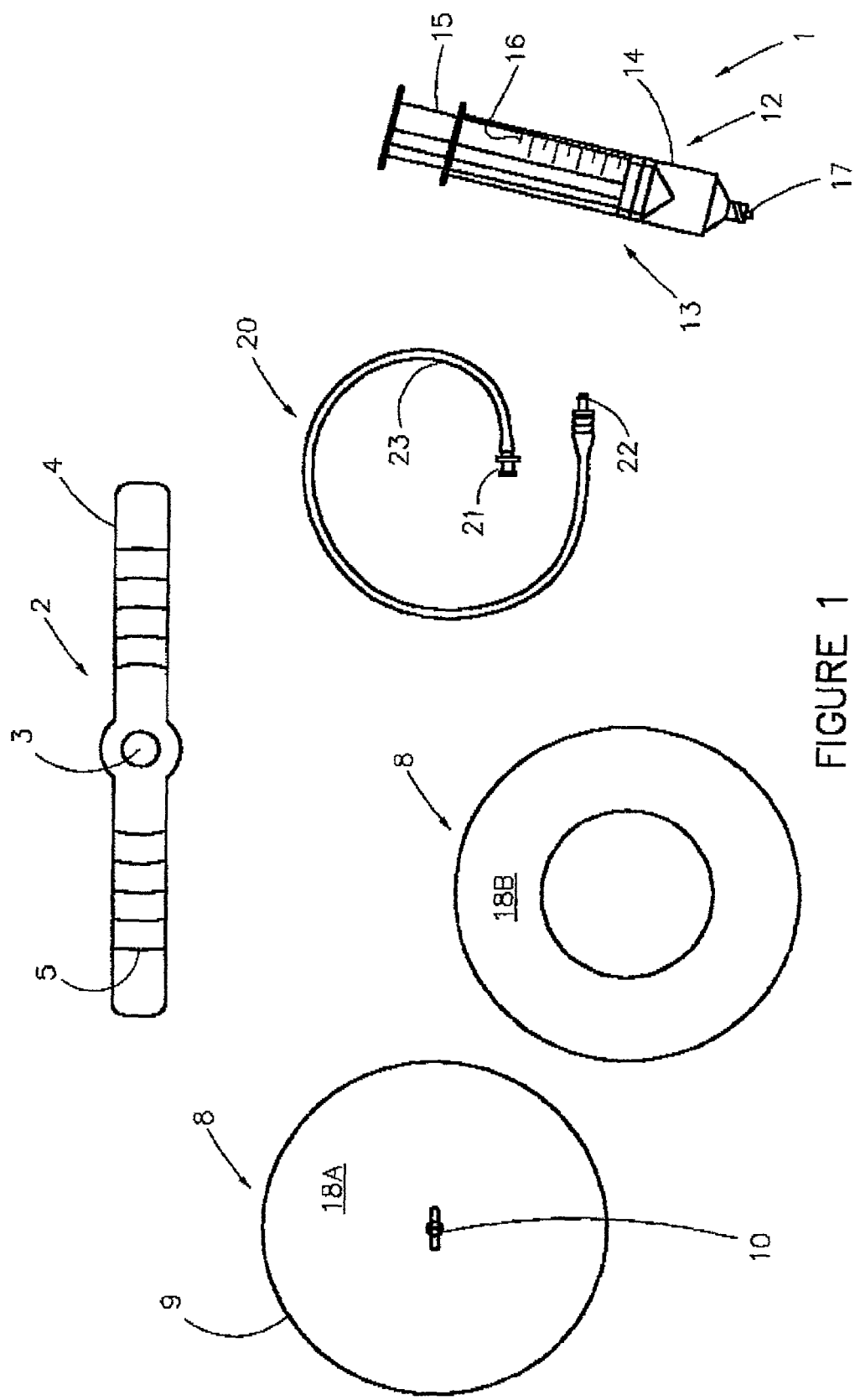
FIG. 1 illustrates the various components of the breast implant sizing system of the present invention.

The main components used in the breast implant sizing method of the present invention are shown in FIG. 1. The components include breast ruler 2, implant devices 8, liquid measuring device 12, and fill tube 20. These components may generally be considered as an integrated breast implant sizing system or kit 1. As used herein, the term "implant devices" includes actual breast implants such as those sold under the trade name Spectrum by Mentor Corporation of Santa Barbara, Calif. However, the definition of "implant devices" for purposes of this disclosure will also include other similarly shaped rubber or plastic pouches which may be filled with liquid and used in the present invention in place of actual breast implants. These pouches will be typically less expensive to manufacture because the pouches are never intended for placement within a human body. The breast implant devices 8 seen in FIG. 1 are actual breast implants 9, with a first side 18A and a second side 18B. A valve 10 will be positioned on side 18A. Valve 10 is a conventional check valve which may be penetrated by an insertion tip or filling needle such that liquid may be injected into breast implant 9, but liquid cannot escape through valve 10 once the filling needle is withdrawn. On the other hand, when using the alternative implant simulating pouches mentioned above, these pouches could have a valve similar to valve 10 or could have any conventional closeable liquid inlet which allows liquid to be inserted into the pouch and then the closing mechanism temporarily sealed so that liquid cannot escape. These variations and all other such variations of implant devices 8 are intended to come within the scope of the present invention.

Figure 4:
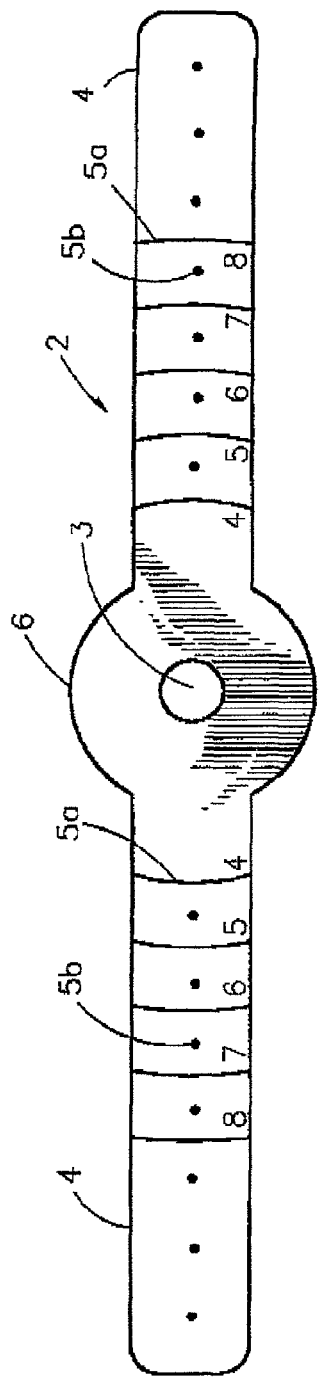
FIG. 4 is a more detailed illustration of the breast ruler.

Breast ruler 2 is best seen in FIG. 4. Breast ruler 2 includes a mid-section 6 with center aperture 3 and two lateral extensions 4 having graduation marks 5a and 5b. Typically aperture 3 will be approximately one centimeter in diameter, but this diameter could vary. As described in more detail below, it is preferred that aperture 3 be large enough in diameter to fit over a human nipple. Graduation marks 5a and 5b will measure the distance in centimeters (lines 5a indicating whole centimeters and dots 5b indicating half centimeters) from the center of aperture 3. Preferably, the lines 5a will have a slight curvature generally corresponding to the curvature at the edge of a human breast. The proper use of breast ruler 2 is illustrated in FIGS. 2 and 3. FIG. 2 shows a female torso 34 with breast 26 and nipple 27 and the breast ruler 2 against breast 26 with center aperture 3 position over nipple 27. Breast ruler 2 is held taunt with one lateral extension 4 pulled toward the sternum and the other lateral extension 4 pulled toward the outside of torso 34. FIG. 3b illustrates the proper positioning of breast ruler 2 being pulled taunt as opposed to the incorrect positioning of breast ruler 2 as seen in FIG. 3a. As suggested in FIGS. 2 and 3b, a proper reading of breast ruler 2 is made by determining which graduation marks 5a or 5b correspond with the inner edge 29 of the breast and the outer edge 28 of the breast.

The purpose of the readings from breast ruler 2 is to aid the user in determining how much fluid to initially place in implant devices 8 before "trying on" the implant devices as described below. Typically, breast ruler 2's reading will be cross-referenced with fluid volume data provided to the user. In a preferred embodiment of the invention, the two readings taken at the inner edge 29 and outer edge 28 are summed to provide a breast width and then compared to a chart such as Table 1.

TABLE 1

| Width (cm) | Volume (cc) |
| --- | --- |
| 11.0 | 225–250 |
| 11.5 | 250–275 |
| 12.0 | 275–300 |
| 12.5 | 300–325 |
| 13.0 | 325–375 |
| 13.5 | 350–400 |
| 14.0 | 375–425 |
| 14.5 | 425–475 |

Figure 5:
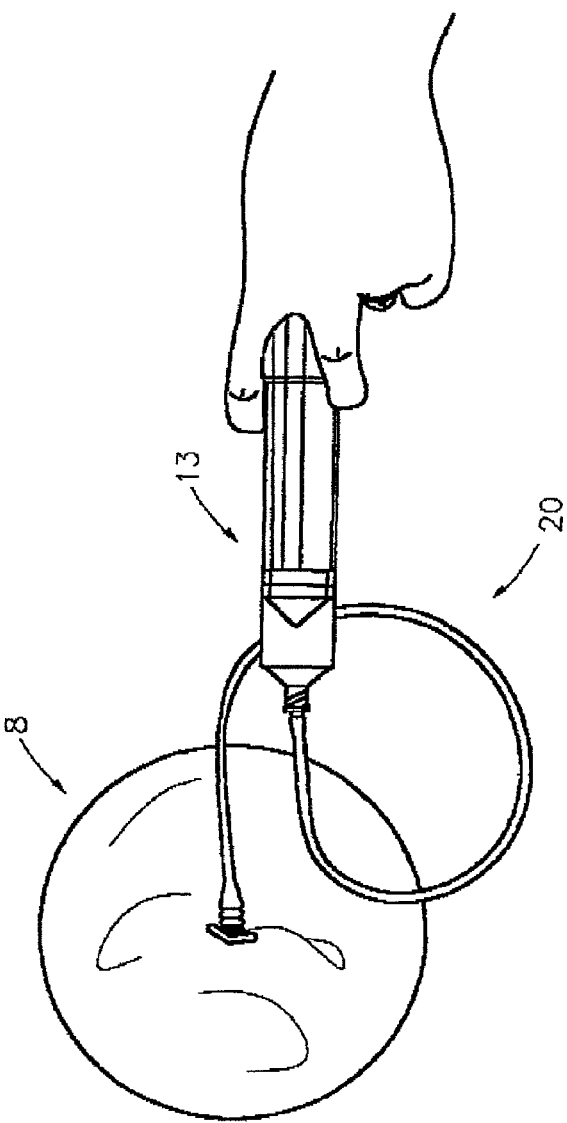
FIG. 5 illustrates the filling of an implant device.

As an example, if it is assumed that the breast ruler shown in FIG. 2 reads 5.5 cm at breast inner edge 29 and 5.5 cm at breast outer edge 28, the resulting sum of 11 cm will suggest the implant devices 8 should be filled with 225 to 250 cc of fluid (e.g. water). The filling of implant device 8 is accomplished with liquid measuring device 12 and fill tube 20. In one preferred embodiment shown in FIGS. 1 and 5, liquid measuring device 12 is a syringe 13. However, any device providing a reliable method of measuring the amount of liquid placed within implant 8 is intended to come within the scope of the present invention. Syringe 13 may be a conventional syringe having a syringe body 14 with graduation marks 16, a syringe plunger 15, and a conventional connector element 17 as is well known in the art. The size of syringe 13 may vary, but a preferred embodiment would have a capacity of about 60 cc. The fill tube 20 will include a short length (e.g. approximately 15 cm) of flexible, hollow tubing having one end a connector 21 for engaging syringe connector 17 on syringe 13, and having a conventional valve insertion tip 22 on the opposite end. In a preferred embodiment, insertion tip 22 may comprise a flexible tube extension which sealingly and fluidly engages valve 10 in order to transmit fluid into breast implants 9.

Figure 6:
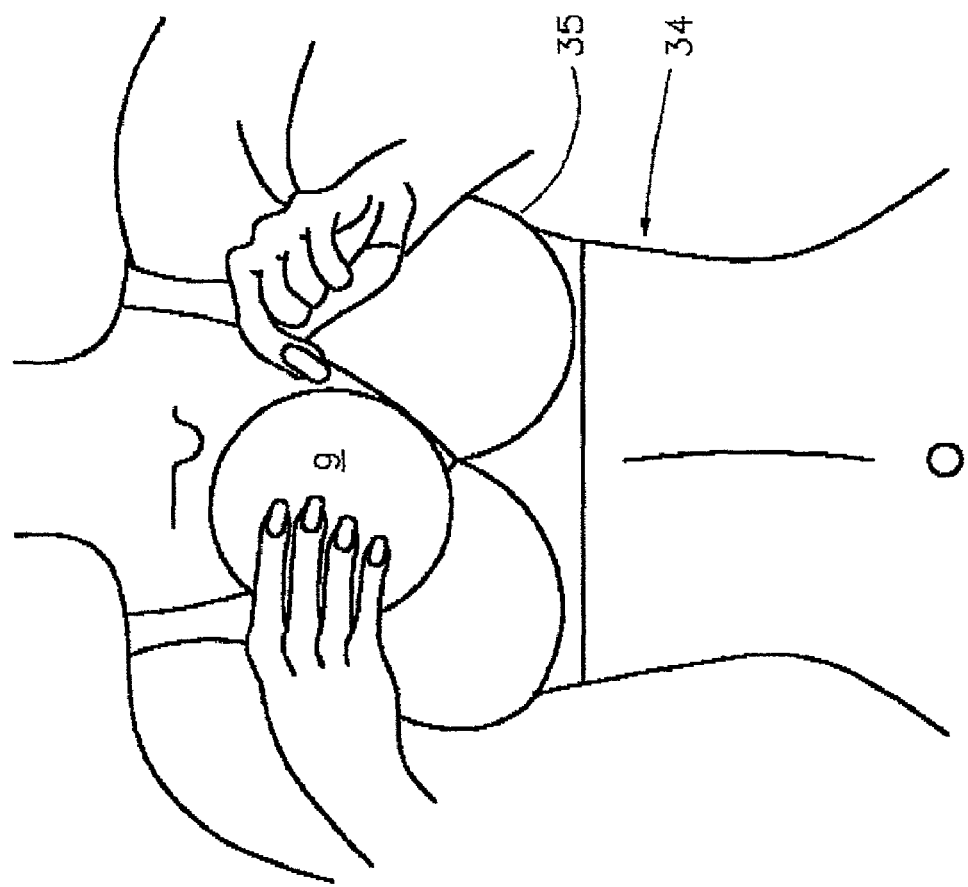
FIG. 6 illustrates the positioning of an implant device under an item of clothing.

In operation, syringe 13 is filled with a given amount of liquid (measured by graduation marks 16) and connector 21 of fill tube 20 is attached to syringe connector 17. Then valve insertion tip 22 on fill tube 20 is inserted into valve 10 of breast implant 9 and the liquid injected into breast implants 9 as suggested in FIG. 5. The process can be repeated until the desired amount of liquid (e.g. that amount set out by Table 1) is injected into breast implants 9. Once the implants 9 are filled with the appropriate amount of liquid, the user will position the implants 9 between her breasts and an article of clothing. As suggested in FIG. 6, each implant 9 may be inserted over the breast between the breast and a bra 35. The user may then put on a lightweight knit shirt or similar tight fitting clothing to observe the appearance of the implants. If the implants appear too small, fluid may be added to implants 9 by using fluid measuring device 12 and fill tube 20 as described above. Likewise, if the implants appear to large, fluid measuring device 12 will be used to remove a measured amount of fluid. The user should keep track of the amount of fluid added and/or subtracted from implants 9. This allows the user to inform the physician of the approximate volume of fluid which renders, in the user's opinion, the most favorable appearance.

In practice, implants 9 placed between the breast and a bra will appear larger than when the same size implant is surgically placed, particularly when the implant is place beneath the chest wall muscle (submuscular) as opposed to beneath the breast tissue (subglandular). Typically, the amount of fluid used in the surgically-placed implant may need to be increased by approximately 15% over the measured amount in order to give it the same appearance as an implant placed between the breast and a bra.

In one embodiment of the present invention, the system would be supplied to users in three versions. Each version would be identical with regard to breast ruler 2, measuring device 12, and fill tube 20. However, the volume of the implant devices 8 would vary among the versions. A height/weight table would assist the user in selecting the correct version. A version may be consider "petite" with an implant device volume range of 200–350 cc; a version considered "regular" with an implant device volume range of 300–450 cc; and a version considered "large" with an implant device volume range of 400–550 cc. In an alternative embodiment, a single version of the system would be provided to the users. However this version would contain at least two pairs of implant devices. The first pair of implant devices would be designed to accommodate the lower volume size range and the second pair of implant devices would be designed to accommodate the higher volume size range. As a still further alternative, a single version of the system could include an even larger number of alternatively sized implants. For example, there could be five sizes of implants: a 250 cc size, a 300 cc size, a 350 cc size, a 400 cc size and a 450 cc size. The system could be provided with a pair of implant devices in each size or only one implant device in each size. In this embodiment (particularly when a pair of implant devices is provided in each size range), it would be feasible to provide sealed implants (i.e. no valve) to which the user would not be required to add or subtract fluid. The user would merely select the best fit from among the five different sizes.

While the foregoing disclosure describes the present invention in terms of a few specific embodiments, the present invention is not limited to these particular configurations. Those skilled in the art will recognize many modifications and variations which may be employed in practicing the present invention. All such modifications and variations are intended to come within the scope of the following claims.

I claim:

1. A method for selecting a properly sized breast implant, said method comprising:

a. providing a breast ruler, at least one pair of flexible, fillable implant devices, and a liquid measuring device adapted to fill said implant devices;

b. wherein said breast ruler is flexible and comprises:

i. a mid-section with a center aperture formed therein; and ii. two lateral extensions extending in opposite directions from said mid-section;

wherein a series of numbered graduation marks are located on each of said lateral extensions, and said numbers increase in magnitude as said graduation marks move away from said center aperture;

c. placing said breast ruler over a breast of a user and measuring a breast width;

d. using said liquid measuring device to fill said implant devices with an approximate amount of liquid corresponding to said breast width;

e. positioning said filled implants over said breasts with an item of clothing; and f. adjusting, as necessary, the amount of liquid in said implant devices and repeating step e.

2. The method according to claim 1, wherein said step of providing a liquid measuring device includes providing a syringe.

3. The method according to claim 1, further providing a fill tube and using said syringe and fill tube to fill said implant devices.

4. The method according to claim 1, further providing a series of recommended implant volumes corresponding to a measurement made with said breast ruler.

5. The method of claim 1, wherein said step of placing said breast ruler over a breast of a user and measuring a breast width includes placing said center aperture of said breast ruler over the nipple of said breast while extending said lateral extensions and noting which graduation marks on said lateral extensions coincide with the inside and outside edges of said breast.

6. A method for selecting a properly sized breast implant, said method comprising:

a. providing a breast ruler and a plurality of flexible implant devices, wherein said plurality of implant devices comprise a set of different sized implant devices and said breast ruler comprises:

i. a mid-section with a center aperture formed therein; and ii. two lateral extensions extending in opposite directions from said mid-section;

wherein a series of numbered graduation marks are located on each of said lateral extensions, and said numbers increase in magnitude as said graduation marks move away from said center aperture;

b. placing said breast ruler over a breast of a user and measuring a breast width;

c. using said breast width from said breast ruler to select a most closely matching implant device from said plurality of implant devices; and d. positioning said implant device over said breast with an item of clothing.

7. The method according to claim 6, wherein said plurality of implant devices comprises a pair of implant devices for each different size of implant device.

8. The method according to claim 6, further providing recommended implant volumes corresponding to a measurement made with said breast ruler.

* * * * *